United States Patent [19]
Guadagni et al.

[11] 4,154,862
[45] May 15, 1979

[54] METHOD OF REDUCING BITTERNESS AND OFF-AFTER-TASTE

[75] Inventors: Dante G. Guadagni, Moraga; Robert M. Horowitz, Pasadena; Bruno Gentili, Glendale; Vincent P. Maier, Newport Beach, all of Calif.

[73] Assignee: The United States of America as represented by the Secretary of Agriculture, Washington, D.C.

[21] Appl. No.: 758,987

[22] Filed: Jan. 13, 1977

Related U.S. Application Data

[63] Continuation-in-part of Ser. No. 587,922, Jun. 18, 1975.

[51] Int. Cl.$^2$ ............................................. A23L 1/226
[52] U.S. Cl. ..................................... 426/536; 426/548
[58] Field of Search ................. 426/599, 534, 51, 616, 426/536, 548

[56] References Cited
PUBLICATIONS
J. Agr. Food Chem., v. 17, No. 4, 1969, 696–700.

*Primary Examiner*—Hiram H. Bernstein
*Attorney, Agent, or Firm*—M. Howard Silverstein; David G. McConnell; Theodore J. Leitereg

[57] ABSTRACT

Bitterness and/or off-after-taste in materials containing substances imparting bitterness and/or off-after-taste thereto are reduced by addition of a minor proportion of neodiosmin.

11 Claims, No Drawings

METHOD OF REDUCING BITTERNESS AND OFF-AFTER-TASTE

CROSS-REFERENCE TO RELATED APPLICATIONS

This is a continuation-in-part of our co-pending application, Ser. No. 587,922, filed June 18, 1975.

BACKGROUND OF THE INVENTION

1. Field of the Invention

This invention relates to and has among its objects the reduction of bitterness due to bitter materials and the reduction of off-after-taste sensations accompanying other compounds added to foods, beverages, or pharmaceutical preparations. A particular object of the invention is the reduction of bitterness due to caffeine, quinine sulfate, and saccharin. Another object of the invention is the reduction of off-after-taste sensations associated with the use of artificial sweetening agents such as saccharin. Further objects of the invention will be evident from the following description wherein parts and percentages are by weight unless otherwise specified. The abbreviation "ppm" used herein refers to parts per million.

2. Description of the Prior Art

Materials containing bitter substances such as limonin (orange juice, etc.), caffeine or other bitter xanthines (coffee, tea, etc.), and quinine or its salts (pharmaceutical preparations) have reduced palatability because they are bitter. Furthermore, foods and beverages containing artificial sweeteners such as saccharin and the like have both a bitterness and an off-after-taste which renders their use as sweeteners less desirable.

Presently, it is common practice to add materials which will mask bitter flavor or off-after-taste occurring in foods, beverages, and pharmaceutical preparations. This method, however, is less than satisfactory because the above condition still exists with equal intensity but, in addition, materials used as maskers also have an affect on the taste quality of the food, beverage, or pharmaceutical preparation. Another method for reducing bitterness and off-after-taste is to add agents which will chemically alter the compounds responsible for the above taste sensations.

SUMMARY OF THE INVENTION

The present invention provides means to obviate the problems outlined above. In accordance with the invention bitterness and off-after-taste sensations are reduced by adding a minor proportion of neodiosmin to materials which exhibit the above taste sensations. The primary advantages of the invention are its effectiveness coupled with its simplicity in that the sole processing required is to mix the neodiosmin with the material containing the components which contribute to bitterness and off-after-taste.

DESCRIPTION OF THE PREFERRED EMBODIMENTS

We have found that when neodiosmin is added to materials which contain bitter compounds a greater amount of the bitter compound is necessary in order to render the material bitter. In order words, a higher concentration of the bitter compound is necessary before an individual can perceive a bitter taste in material containing neodiosmin as compared with a material that does not contain neodiosmin. Similarly, when neodiosmin is added to materials which exhibit an off-after-taste due to the addition thereto of a compound that produces such an after-taste, a greater amount of the latter compound is necessary in order to produce the same intensity of off-after-taste.

It is to be emphasized that neodiosmin operates by suppressing the perception of bitterness and off-after-taste. Thus, when neodiosmin is added to materials containing compounds which cause bitterness and off-after-taste, the material will taste less bitter, or have less of an off-after-taste, than the same material to which neodiosmin had not been added. Unlike prior methods for reducing bitterness or off-after-taste, the invention does not involve chemical alternation of the compound responsible for bitterness or off-after-taste. It is further to be observed that neodiosmin does not operate by any masking action, because neodiosmin itself is tasteless and odorless.

The amount of neodiosmin to be added to the material will depend on various factors such as the nature of the material, the concentration therein of the compound or compounds responsible for bitterness and off-after-taste, and the degree of suppression desired. In any particular case, the proper amount of neodiosmin to be added can be readily determined by pilot trials. In any event, only a very minor amount of neodiosmin is needed. Thus, in general, it has been found that useful results are obtained by adding about 10 to 150 ppm of neodiosmin based on the weight of the material to be treated. The material of reduced bitterness or reduced off-after-taste is prepared simply by incorporating the added neodiosmin therewith.

Neodiosmin is a known compound. The synthesis thereof by oxidation of neohesperidin is disclosed by Horowitz and Gentili, Journal of Agricultural & Food Chemistry, Vol. 17, at page 698 (1969). The structure of neodiosmin is

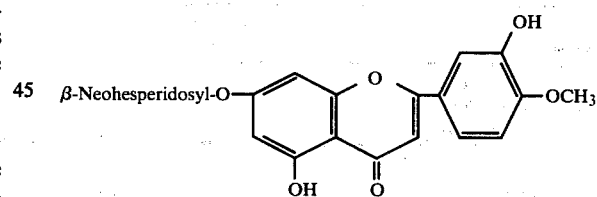

wherein β-Neohesperidosyl is 2-0-α-L-rhamnopyranosly-β-D-glucopyranosyl.

The invention is of wide versatility and can be used to reduce bitterness caused by a number of compounds such as limonin, naringin, quinine and its salts, e.g., quinine sulfate and quinine hydrochloride, nicotine, xanthines, e.g., caffeine and the like, urea, magnesium sulfate, sodium benzoate, neohesperidin, saccharin, and the like.

More importantly the invention can be used to suppress off-after-taste sensations such as those accompanying artificial sweeteners, e.g., saccharin, neohesperidin dihydrochalcone, and so forth.

EXAMPLES

The invention is further demonstrated by the following illustrative examples.

EXAMPLE 1

Reduction of Bitterness Due to Caffeine

Judges (40) experienced in tasting bitter constituents were presented with completely randomized paired samples of water solutions containing varying amounts of caffeine on the one hand and caffeine plus neodiosmin on the other. The taste thresholds of the two different solutions were determined in this manner and found to be the following:

| Sample | Taste Threshold of Caffeine (ppm) |
| --- | --- |
| Water plus caffeine plus 10 ppm neodiosmin | 230 |
| Water plus caffeine | 128 |

The effect of neodiosmin on the bitterness of caffeine was also evaluated and is represented in the table below.

| Sample | Evaluation* |
| --- | --- |
| Water plus 100 ppm caffeine plus 10 ppm neodiosmin | Not bitter |
| Water plus 200 ppm caffeine plus 20 ppm neodiosmin | Not bitter |
| Water plus 200 ppm caffeine plus 10 ppm neodiosmin | Bitter |
| Water plus 100 ppm caffeine | Bitter |
| Water plus 200 ppm caffeine | Very bitter |

*Samples were evaluated as not bitter, bitter, very bitter, and extremely bitter.

EXAMPLE 2

Reduction of Bitterness Due to Quinine Sulfate

The taste thresholds of the solutions were determined as described in Example 1.

| Sample | Taste Threshold of Quinine Sulfate (ppm) |
| --- | --- |
| Water plus quinine sulfate plus 10 ppm neodiosmin | 9.5 |
| Water plus quinine sulfate | 4.0 |

The effect of neodiosmin on the bitterness of quinine sulfate was also evaluated as described in Example 1.

| Sample | Evaluation |
| --- | --- |
| Water plus 4 ppm quinine sulfate plus 10 ppm neodiosmin | Not bitter |
| Water plus 8 ppm quinine sulfate plus 10 ppm neodiosmin | Not bitter |
| Water plus 8 ppm quinine sulfate plus 20 ppm neodiosmin | Not bitter |
| Water plus 4 ppm quinine sulfate | Bitter |
| Water plus 8 ppm quinine sulfate | Extremely bitter |

EXAMPLE 3

Reduction of Off-after-taste and Bitterness Due to Saccharin

A panel of judges (40) trained in tasting bitter constituents and off-after-taste materials were asked to compare samples containing water, saccharin, and neodiosmin with samples containing only water and saccharin. The samples were known to the panel only by code numbers. The judges were asked to indicate which sample was less bitter and had the least off-after-taste.

Comparison A: Water containing 20 ppm saccharin plus 10 ppm neodiosmin was compared with water containing only 20 ppm saccharin. The results were that 30 of the judges (75% of the panel) decided that the water with added neodiosmin was less bitter and had less off-after-taste than the control, i.e., water plus 20 ppm saccharin without added neodiosmin.

Comparison B: Water containing 40 ppm saccharin plus 10 ppm neodiosmin was compared with water containing only 40 ppm saccharin. In this comparison 75% of the panel favored, as being less bitter and having less off-after-taste, the water with added neodiosmin over that which did not contain neodiosmin.

Comparison C: Water containing 80 ppm saccharin plus 20 ppm neodiosmin was compared with water containing only 80 ppm saccharin; 70% of the judges selected the former as being less bitter and having less off-after-taste than the latter.

Having thus described our invention, we claim:

1. A process for reducing bitterness in orally-ingested materials containing bitter substances, which comprises adding to the material an amount of neodiosmin sufficient to reduce the bitterness therein.
2. The process of claim 1 wherein the material is a beverage.
3. The process of claim 1 wherein the material is a food.
4. The process of claim 1 wherein the amount of added neodiosmin is about from 10 to 150 ppm.
5. The process of claim 1 wherein the material contains as the bitter substance caffeine.
6. The process of claim 1 wherein the material contains as the bitter substance a quinine salt.
7. The process of claim 1 wherein the material contains as the bitter substance an artificial sweetening agent.
8. The process of claim 7 wherein the artificial sweetening agent is saccharin.
9. The process of claim 1 wherein both bitterness and off-after-taste in materials containing substances which impart bitterness and off-after-taste thereto are reduced by adding to the material an amount of neodiosmin sufficient to reduce the bitterness and off-after-taste therein.
10. The process of claim 9 wherein the substance imparting both bitterness and off-after-taste is an artificial sweetening agent.
11. The process of claim 1 wherein the material is an oral pharmaceutical preparation.

* * * * *